(12) United States Patent
Drenker et al.

(10) Patent No.: US 7,309,862 B2
(45) Date of Patent: *Dec. 18, 2007

(54) METHOD FOR MARKING SITES

(75) Inventors: Karl-Heinz Drenker, Solingen (DE); Hans-Jörg Seiler, Leverkusen (DE); Volker Kahle, Bergisch Gladbach (DE); Norbert Donkels, Mönchengladbach (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/518,637

(22) Filed: Sep. 11, 2006

(65) Prior Publication Data

US 2007/0057181 A1 Mar. 15, 2007

Related U.S. Application Data

(62) Division of application No. 10/817,985, filed on Apr. 5, 2004, now Pat. No. 7,126,119.

(51) Int. Cl.
 *G01T 1/161* (2006.01)
(52) U.S. Cl. .................. 250/302; 250/301; 250/372
(58) Field of Classification Search ............. 250/302, 250/372
See application file for complete search history.

(56) References Cited

U.S. PATENT DOCUMENTS

| 3,995,157 A | 11/1976 | Holub et al. ............. 250/302 |
| 4,745,276 A | 5/1988 | Broicher et al. |
| 6,476,385 B1 | 11/2002 | Albert ....................... 250/302 |
| 2002/0165294 A1 | 11/2002 | Cooper et al. |
| 2002/0178970 A1 | 12/2002 | Fox et al. ............... 106/31.64 |
| 2003/0232885 A1* | 12/2003 | Raczek et al. ............ 514/557 |

FOREIGN PATENT DOCUMENTS

| DE | 19521500 | 6/1996 |
| EP | 0324583 | 10/1994 |
| GB | 2376038 | 12/2002 |

OTHER PUBLICATIONS

Houben-Weyl, Methoden der organischen Chemie (Methods of organic chemistry), 4th Edition, vol. E 20, Part 2, pp. 1178-1191 Homopolymerisation.
Houben-Weyl, Methoden der organischen Chemie (Methods of organic chemistry), 4th Edition, vol. E 20, Part 2, pp. 1150-1155; Markert G., "1.1.3.1. Polymerisationsverfahren".
Houben-Weyl, Methoden der organischen Chemie (Methods of organic chemistry), 4th Edition, vol. E 20, Part 2, pp. 985; "2.2.1. mit Acrylsaure-estern bzw. Acrysaure-Salzen" "2.2.2 mit Methacrysaure-methylester".
Houben-Weyl, Methoden der organischen Chemie (Methods of organic chemistry), 4th Edition, vol. E 20, Part 1, pp. 1659-1681; "1.6. Zweiphasen-Systeme" and 1.6.1 Poly(urethane)-Dispersionen in Wasser.
Houben-Weyl, Methoden der organischen Chemie (Methods of organic chemistry), 4th Edition, vol. E 20, Part 2, pp. 1195-1226; "1. Homopolymerisation".
Houben-Weyl, Methoden der organischen Chemie (Methods of organic chemistry), 4th Edition, vol. E 20, Part 3, pp. 2151-2161.
Houben-Weyl, Methoden der organischen Chemie (Methods of organic chemistry), 4th Edition, vol. E 20, Part 3, pp. 2138-2147.
Houben-Weyl, Methoden der organischen Chemie (Methods of organic chemistry), 4th Edition, vol. E 20, Part 3, p. 2151.
Houben-Weyl, Methoden der organischen Chemie (Methods of organic chemistry), 4th Edition, vol. E 20, Part 3, pp. 2086-2089.
Houben-Weyl, Methoden der organischen Chemie (Methods of organic chemistry), 4th Edition, vol. E 20, Part 3, p. 2092.
Houben-Weyl, Methoden der organischen Chemie (Methods of organic chemistry), 4th Edition, vol. E 20, Part 3, pp. 2093-2123.
DGMK-Fachbereich Kohlenveredlung [DGMK coal conversion department, "Herstellung and Anwendung mehrkemiger Aromaten und Heteroaromaten [Production and use of polymuclear aromatics and heteroaromatics]", Nov. 28, 1991 in Bochum, pp. 95-118.

* cited by examiner

*Primary Examiner*—David Porta
*Assistant Examiner*—Marcus H Taningco
(74) *Attorney, Agent, or Firm*—Michael A. Miller

(57) ABSTRACT

A method for determining changes of a site, wherein the site is treated with an aqueous dispersion having at least one binder, at least one substance emitting visible light on UV exposure, at least one binder and, optionally, a dispersant and the site thus treated and/or untreated adjacent sites are exposed to UV light and the deviation of the light intensity of the emitted light of a partial area of the site from the mean light intensity of the emitted light of the site area and/or the light intensity of the emitted light of a part of the adjacent, untreated area from the mean light intensity of the emitted light of the adjacent untreated areas and/or the light intensity of the emitted light of the site immediately after the treatment with the composition from the light intensity of the emitted light at a later time and/or the light intensity of the emitted light of the adjacent untreated area immediately after the treatment of the site with the composition from the light intensity of the emitted light of the adjacent, untreated area at a later time are determined.

11 Claims, No Drawings

METHOD FOR MARKING SITES

This application is a Divisional of U.S. patent application Ser. No. 10/817,985 filed Apr. 5, 2004, now U.S. Pat. No. 7,126,119 entitled "Method for Marking Sites", the contents of which are hereby incorporated by reference in their entirety.

The present invention relates to a method for marking sites, in particular for the purpose of determining access on foot, access by vehicle and/or other manipulations.

The use of the abovementioned method relates primarily to areas which can be completely monitored only at high cost, for example by a large number of guards, or protected by expensive fences. The method according to the invention is distinguished by wide applicability and high flexibility. In addition few personnel are required for the method according to the invention.

The invention relates to a method for determining changes of a site, which is characterized in that
a) the site is treated with a composition and
b) the site thus treated and/or the untreated areas adjacent thereto are exposed to UV light and the deviation
   b1) of the light intensity of the emitted light of a partial area of the site from the mean light intensity of the emitted light of the site area and/or
   b2) the light intensity of the emitted light of a part of the adjacent, untreated area from the mean light intensity of the emitted light of the adjacent untreated areas and/or
   b3) the light intensity of the emitted light of the site immediately after the treatment with the composition from the light intensity of the emitted light at a later time and/or
   b4) the light intensity of the emitted light of the adjacent untreated area immediately after the treatment of the site with the composition from the light intensity of the emitted light of the adjacent, untreated area at a later time
are determined,
the composition being an aqueous dispersion comprising:
a1) at least one binder,
a2) at least one substance emitting visible light on UV exposure and
a3) optionally a dispersant.

Aqueous polymer formulations which contain substances which emit visible light on UV exposure have long been known in various applications.

DE-A 19 521 500 describes an aqueous dispersion comprising a water-dispersible polyurethane and a fluorescent dye as a coating material for greenhouse sheets.

U.S. Pat. No. 3,995,157 describes a method for discovering damage (breaks, cracks, etc.) in metallic objects which functions by means of applying a coating consisting of a polymeric material and a compound fluorescing on UV exposure.

The composition preferably contains polymeric film-forming compounds as binders of component a1).

Binders of component a1) can be prepared by polymerization in aqueous solution, such as, for example, acrylamido homo- and copolymers, which are described in Houben-Weyl, Methoden der organischen Chemie [Methods of organic chemistry], 4th Edition, Volume E 20, Part 2, pages 1178-1191. Examples of suitable comonomers for acrylamide and methacrylamide are: styrene, acrylic acid and methyl, ethyl, butyl and 2-ethylhexyl (meth)acrylate, either alone or as a mixture of a plurality of comonomers.

The comonomers are used in numerical ratios which are known to a person skilled in the art.

Emulsion polymers as described in Houben-Weyl, Methoden der organischen Chemie [Methods of organic chemistry], 4th Edition, Volume E 20, Part 2, pages 1150 to 1155, are furthermore suitable as products of the copolymerization of methyl, ethyl, butyl and 2-ethylhexyl (meth)acrylate with styrene, acrylonitrile, acrylic acid, acrylamide and methacrylamide, either alone or as a mixture with a plurality of comonomers.

Copolymers, such as water-soluble styrene/acrylic acid or methyl, ethyl, butyl and 2-ethylhexyl (meth)acrylate, as described in Houben-Weyl, Methoden der organischen Chemie [Methods of organic chemistry], 4th Edition, Volume E 20, Part 2, page 985, and styrene/maleic acid copolymers, which are described in the same reference, are also suitable.

Preferred binders of component a1) are polyurethanes, as described in Houben-Weyl, Methoden der organischen Chemie [Methods of organic chemistry], 4th Edition, Volume E 20, Part 1, pages 1659 to 1681.

Particularly preferred polyurethanes as binders of component a1) are those which are dispersible in water itself and are prepared from:
i) diisocyanates comprising 4 to 50 carbon atoms,
ii) diols having a molecular weight of 500 to 4000 g/mol,
iii) diols and/or di- and triamines as chain extenders having a molecular weight of 62 to 500 g/mol,
iv) mono- and polyols and/or mono- and polyamines having primary and/or secondary amino groups, which also have a group having a hydrophilizing effect.

Examples of suitable diisocyanates i) are: tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, trimethylhexane diisocyanate or tetramethylhexane diisocyanate, cycloaliphatic diisocyanates, such as 1,4-, 1,3- or 1,2-diisocyanatocyclohexane, 4,4'-di(isocyanatohexyl)methane, 1-isocyanato-3,3,5-trimethyl-5-(isocyanatomethyl)-cyclohexane (isophorone diisocyanate) or 2,4- or 2,6-diisocyanato-1-methylcyclohexane, and aromatic diisocyanates, such as 2,4- or 2,6-toluene diisocyanate, tetramethylxylylene diisocyanate, p-xylylene diisocyanate, 2,4'- or 4,4'-diisocyanatodiphenylmethane, 1,3- or 1,4-phenylene diisocyanate, 1-chloro-2,4-phenylene diisocyanate, 1,5-naphthylene diisocyanate, diphenylene 4,4'-diisocyanate, 4,4'-diisocyanato-3,3'-dimethylbiphenyl, 3-methyldiphenylmethane 4,4'-diisocyanate or diphenyl ether 4,4'-diisocyanate. Mixtures of said diisocyanates may also be present.

Preferred diisocyanates (i) are the industrial polyisocyanates customary in polyurethane chemistry, such as hexamethylene diisocyanate, 1-isocyanato-3,3,5-trimethyl-5-isocyanatomethylcyclohexane (isophorone diisocyanate, IPDI), perhydro-4,4'-diphenylmethane diisocyanate, 2,4- and 2,6-toluene diisocyanate and any desired mixtures of these isomers, diphenylmethane 4,4'-diisocyanate and mixtures thereof with the corresponding 2,2'- and 2,4'-isomers.

The abovementioned aliphatic polyisocyanates are particularly preferred.

The diols ii) have an average molecular weight of 500 to 4000 g/mol, preferably of 500 to 3000 and particularly preferably of 700 to 3000 g/mol and have a functionality of 2.

Polyesterdiols (ii) are prepared by reacting polyhydric alcohols with dibasic carboxylic acids. Instead of the carboxylic acids, carboxylic anhydrides may also be used. Both aliphatic and cycloaliphatic, and araliphatic and aromatic dicarboxylic acids can be used. Moreover, heterocyclic, unsaturated or substituted (for example by halogen atoms) dicarboxylic acids may be used. The following may be mentioned by way of examples of these: malonic acid, succinic acid, glutaric acid, adipic acid, pimelic acid, suberic acid, azelaic acid, sebacic acid, nonanedicarboxylic acid, decanedicarboxylic acid, undecanedicarboxylic acid, phthalic acid, isophthalic acid, terephthalic acid, phthalic anhydride, tetrahydrophthalic anhydride, glutaric anhydride, succinic anhydride, maleic acid, maleic anhydride, fumaric acid and dimeric fatty acids.

Preferred dicarboxylic acids are those which have 2 to 20 carbons taking into account the carboxyl carbons.

Examples of suitable polyhydric alcohols are: ethylene glycol, propane-1,2-diol, propane-1,3-diol, butane-1,4-diol, butene-1,4-diol, butyne-1,4-diol, pentane-1,5-diol, neopentylglycol, diethylene glycol, triethylene glycol, tetraethylene glycol, polyethylene glycols, dipropylene glycol, tripropylene glycol, polypropylene glycols, dibutylene glycol and also polybutylene glycols.

Ethylene glycol, butane-1,4-diol, hexane-1,6-diol, neopentylglycol, octane-1,8-diol and dodecane-1,12-diol are preferred.

In addition, reaction products of the diols listed above with phosgene or their transesterification products with carbonic esters, such as, for example, diphenyl carbonate, can likewise be used as polyesterdiols (ii).

Bishydroxy-functional products of the ring-opening polymerization of cyclic esters, such as, for example, of butyrolactone or caprolactone, can also be used as polyesterdiols (ii).

Polyetherdiols (ii) are obtainable, for example, by reaction of ethylene oxide, propylene oxide, styrene oxide and/or butylene oxide with water or with other low molecular weight initiator molecules, such as, for example, ethylene glycol, propane-1,2-diol, propane-1,3-diol, butane-1,4-diol, butene-1,4-diol, butyne-1,4-diol, pentane-1,5-diol, neopentylglycol, diethylene glycol, triethylene glycol, tetraethylene glycol, polyethylene glycols, dipropylene glycol, tripropylene glycol, polypropylene glycols, dibutylene glycol and also polybutylene glycols, by known processes of the prior art.

Where the field of use requires a biodegradable polyester dispersion, polyesterdiols are preferred as diols (ii).

Polyols (iii) which are suitable as chain extenders, optionally also as crosslinking agents, are, for example, low molecular weight polyhydric alcohols having a molecular weight range from 62 to 400 g/mol. The following diols may be used: ethylene glycol, propane-1,2-diol, propane-1,3-diol, butane-1,4-diol, butene-1,4-diol, butyne-1,4-diol, pentane-1,5-diol, neopentylglycol, diethylene glycol, triethylene glycol, tetraethylene glycol, polyethylene glycols, dipropylene glycol, tripropylene glycol, polypropylene glycols, dibutylene glycol and also polybutylene glycols.

Ethylene glycol, butane-1,4-diol, hexane-1,6-diol, neopentylglycol, octane-1,8-diol and dodecane-1,12-diol are preferred.

If branching is desired, it is also possible to use polyols having a higher functionality, such as, for example, trimethylolpropane, glycerol, pentaerythritol, sorbitol or sucrose.

Di- or triamines can be employed as amines (iii) which can be used as chain extenders, optionally also as crosslinking agents. These preferably have a molecular weight of 60 to 300 g/mol and are used, especially in crosslinking and/or chain extension, in water. For example, the following are suitable: 1,4-diaminobenzene, 2,4- and 2,6-diaminotoluene, 2,4'- and/or 4,4'-diaminodiphenylmethane, 1,4-diaminobutane, 1,6-diaminohexane, ethylenediamine and its homologs, isophoronediamine, bis(4-aminocyclohexyl)-methane, 1,4-diaminocyclohexane, hydrazine, hydrazine hydrate and piperazine.

An example of the trifunctional amines is diethylenetriamine.

Particularly preferred diamines are aliphatic types, such as, for example, 1,4-diaminobutane, 1,6-diaminohexane, isophoronediamine, bis-(4-aminocyclohexyl)-methane, 1,4-diaminocyclohexane, ethylenediamine and its homologs and piperazine.

The less preferred diamines include compounds such as 2,4-diaminomesitylene, 1,3,5-triethyl-2,4-diaminobenzene, 1,3,5-triisopropyl-2,4-diaminobenzene, 1-methyl-3,5-diethyl-2,4-diaminobenzene, the industrial mixtures thereof with 1-methyl-3,5-diethyl-2,6-diaminobenzene, 4,6-dimethyl-2-ethyl-1,3-diaminobenzene, 3,5,3',5'-tetraethyl-4,4'-diaminodiphenylmethane, 3,5,3',5'-tetraisopropyl-4,4'-diaminodiphenylmethane or 3,5-diethyl-3',5'-diisopropyl-4,4'-diaminodiphenylmethane.

Any desired mixtures of such diamines may also be used.

Polyols and/or polyamines (iv) having primary and/or secondary amino groups, which also have a group having a hydrophilizing effect, are used for ensuring the water dispersibility of the polyurethane.

The amount to be used of groups having a hydrophilizing effect is known to a person skilled in the art; the amount which ensures sufficient water dispersibility of the polyurethane is always used.

Examples of suitable groups having a hydrophilizing effect are:

a) nonionic structures of the general formula (I):

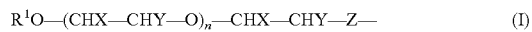

in which n represents a number from 3 to 70,

X and Y denote hydrogen or methyl, and, where one of the radicals X or Y represents methyl, the other must be hydrogen, $R^1$ denotes a straight-chain or branched $C_1$-$C_6$-alkyl radical or straight-chain or branched $C_1$-$C_6$-acyl radical, it furthermore being possible for $R^1$ also to form a cyclic —$(CH_2)_m$-alkylene radical with m=4, 5, 6 or 7, in which one or two $CH_2$ groups can be replaced by O and/or NH, and/or one or two $CH_2$ groups can be substituted by methyl, and Z represents O, S or NH and ensures connection to the polyurethane;

b) cationic structures of the general formula (II):

in which

X and Y denote hydrogen or methyl and $R^2$ and $R^3$ represent straight-chain or branched alkyl radicals, via which the connection to the cationic polyurethane is ensured;

c) anionic structures from the group consisting of: sulphonate, carboxylate, phosphate in the form of their alkali metal and/or ammonium salts.

Particularly suitable mono- and polyols and/or mono- and polyamines (iv) having nonionic groups are polyethylene glycol monoalkyl ethers, which are advantageously used in the preparation of the polyurethane and before the dispersing and act as chain terminators.

Polyethylene glycol monomethyl ethers are particularly preferred.

Examples of particularly suitable mono- and polyamines (iv) having potentially cationic groups, which can be cationized by protonation with acids and/or quaternization by means of alkylating agents, are N,N-bishydroxyalkylalkylamine, N-alkyldialkanolamines, trishydroxyalkylamines, N,N-dialkylalkylamines, dialkyl alcohols; here, the alkyl radicals must comprise one to four carbon atoms.

N-Methyldiethanolamine, N-ethyldiethanolamine, N-butyldiethanolamine, dimethylethanolamine, diethylethanolamine and triethanolamine are particularly preferred.

Examples of particularly suitable mono- and polyols and/or mono- and polyamines (iv) having potentially anionic groups, which can be anionized by salt formation with ammonia or alkali metal hydroxides, carbonates and/or bicarbonates, are mono- and dihydroxycarboxylic acids, mono- and diaminocarboxylic acids, mono- and diaminosulphonic acids and mono- and dihydroxysulphonic acids.

Lactic acid, dimethylolpropionic acid, glycocoll, taurine and 2-(2-aminoethyl)ethanesulphonic acid are particularly preferred.

The preparation of the dispersions is effected, for example, according to the rules of the prior art (Houben-Weyl, Methoden der organischen Chemie [Methods of organic chemistry], 4th Edition, Volume E 20, Part 1, pages 1659 to 1681), either by the acetone method or by the melt dispersion method.

The hydroxy-functional components (iv) can advantageously be incorporated into the polyurethane prior to dispersing, and the amino-functional components (iv) are expediently added to the dispersing water in the preparation of the dispersion.

In the case of components (iv) containing potentially cationic groups, the dispersing water is acidified according to the content of component (iv) in the polyurethane; in the case of potentially anionic components (iv), alkali is added to the dispersing water according to the content of the component (iv) in the polyurethane.

Examples of a suitable substance b) emitting visible light on UV exposure are optical brighteners, also referred to as fluorescent whitening agents. The optical brighteners which can be used for the purpose according to the invention preferably absorb light in a wavelength from 1 nm to 420 nm, preferably 200 to 420 nm, and emit light preferably in the wavelength interval between 360 and 830 nm. The main absorption peak is at a lower wavelength than the main emission peak.

A mixture according to the invention preferably contains 0.001 to 20% by weight, preferably 0.01 to 10% by weight, of the optical brightener.

The optical brighteners which can preferably be used for the application according to the invention belong, for example, to the following structure classes: polystyrylstilbenes, flavonic acid derivatives, coumarins or pyrazolines.

Polystyrylstilbenes preferably have one or more structural units of the formula (III)

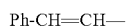  (III).

Here, Ph is intended to represent a phenyl radical.

They can be characterized in particular by the formula (IV):

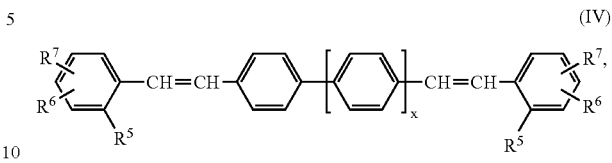

in which
$R^5$ denotes hydrogen, hydroxyl, $SO_3M$, COOM, $OSO_3M$ or OPO(OH)OM, and M represents hydrogen, Na, K, Ca, Mg, ammonium, mono-, di-, tri- or tetra-$C_1$-$C_{30}$-alkylammonium, mono-, di-, tri- or tetra-$C_1$-$C_{30}$-hydroxyalkylammonium or ammonium di- or trisubstituted by mixtures of $C_1$-$C_{30}$-alkyl and $C_1$-$C_{30}$-hydroxyalkyl groups, $SO_2N(C_1$-$C_{30}$-alkyl$)_2$, O—(-$C_1$-$C_{30}$-alkyl), CN, Cl, COO(-$C_1$-$C_{30}$-alkyl), CON(-$C_1$-$C_{30}$-alkyl$)_2$ or a $C_1$-$C_{30}$-alkyl radical,
$R^6$ and $R^7$, independently of one another, denote $SO_3M$, COOM, $OSO_3M$ or OPO(OH)OM and M has the meaning described above, x has the value 0 or 1 and the structure (III) is trans-coplanar or cis-coplanar.

Flavonic acid derivatives:

A preferred generally valid structure is described by the formula (V):

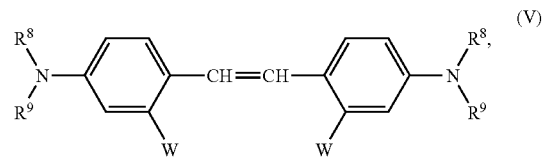

in which
$R^8$ denotes hydrogen, $R^9$ denotes a mono- or disubstituted triazine ring and
W represents an anionic function, such as, for example, carboxylate, sulphate, sulphonate or phosphate,
M having the above meaning.

Preferred brighteners of the formula (V) are those which correspond to the formula (VI)

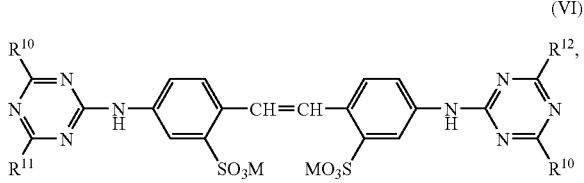

in which
$R^{10}$, $R^{11}$ and $R^{12}$, independently of one another, denote phenoxy, mono- or disulphonated phenoxy, phenylamino, mono- or disulphonated phenylamino, phenylamino substituted by $C_1$-$C_3$-alkyl, cyano, halogen, COOR, CONH—R, —NH—COR, $SO_2NH$—R, O—R, morpholino, piperidino, pyrrolidino, —O—$C_1$-$C_4$-alkyl, —NH($C_1$-$C_4$-alkyl), —NH($C_1$-$C_4$-alkyl$)_2$, —NH—$C_2$-$C_4$-alkylene-O—$C_2$-$C_4$-alkylene-OR, —NH($C_2$-$C_4$-hydroxyalkl)$_2$, —NHC$_2$-C$_4$-akylene-=-C$_2$-C$_4$-alkylene-OR, an amino acid or an amino acid amide from the amino group of which a hydrogen atom has been removed; —NHCH$_2$CH$_2$OH, —N(CH$_2$CH$_2$OH)$_2$, —N(CH)$_3$CH$_2$CH$_2$OH, —NH$_2$, —CH$_3$, —S—C$_1$-C$_4$-alkyl, —S-aryl, —Cl, —NHCH$_2$CH$_2$SO$_3$H, —NH(CH$_2$CH$_2$SO$_3$H)$_2$, —N(CH$_2$CH$_2$OH)CH$_2$CH$_2$CONH$_2$; and R represents H or C$_1$-C$_3$-alkyl and M has the meaning described above.

Brighteners of the formula (V) which correspond to the formula (VIII)

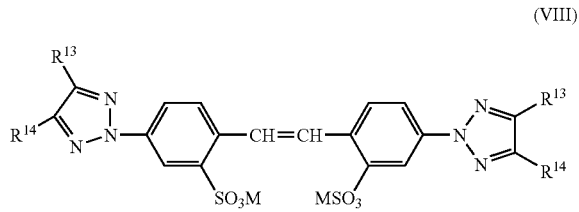

(VIII)

in which
R$^{13}$ and R$^{14}$, independently of one another, are hydrogen, phenyl, monosulphonated phenyl, methyl, ethyl, propyl, methoxy or ethoxy and M has the above meaning, are likewise preferred.

Coumarins:
Preferred coumarins are, for example, those of the formula (IX):

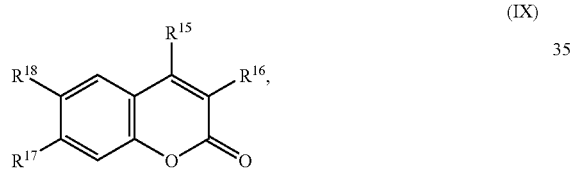

(IX)

in which radical R$^{15}$ represents (CH$_2$)$_{1-4}$COOM, (CH$_2$)$_{1-4}$SO$_3$M, (CH$_2$)$_{1-4}$SO$_4$M or (CH$_2$)$_{1-4}$OPO(OH)OM, with M as described above,
R$^{16}$ represents H, phenyl, COO-C$_1$-C$_{30}$-alkyl or glucosyl,
R$^{17}$ denotes OH or O—C$_1$-C$_{30}$-alkyl and
R$^{18}$ denotes OH, O—C$_1$-C$_{30}$-alkyl or glycosidically bonded sugar radicals.

Pyrazolines:
The preferred pyrazolines which can be used in the application according to the invention are, for example, those of the formula (X):

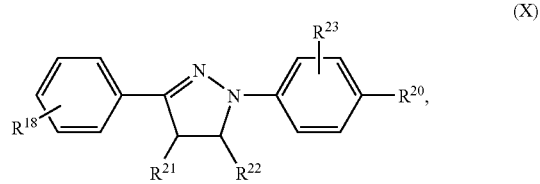

(X)

in which
R$^{19}$ denotes hydrogen or Cl,
R$^{20}$ denotes SO$_3$M, COOM, OSO$_3$M or OPO(OH)OM, the definitions above applying to M,
R$^{21}$ and R$^{22}$, independently of one another, denote hydrogen, C$_1$-C$_{30}$-alkyl or phenyl, and
R$^{23}$ denotes hydrogen or Cl.

In addition to the specified optical brighteners which are colourless as substances, it is also possible to use so-called fluorescent dyes, as published, for example, by H. Langhals and described in conference volume: DGMK-Fachbereich Kohlenveredlung [DGMK coal conversion department], meeting on "Herstellung und Anwendung mehrkerniger Aromaten und Heteroaromaten [Production and use of polynuclear aromatics and heteroaromatics]", 28 Nov. 1991 in Bochum, on pages 95 to 118, provided that this does not impair the intended use or the natural colour on an appropriate surface is inconspicuous. The compounds mentioned there are not preferred, however.

Preferred as substance a2) emitting visible light on UV exposure are the triazine derivatives of flavonic acid having the following structure (XI).

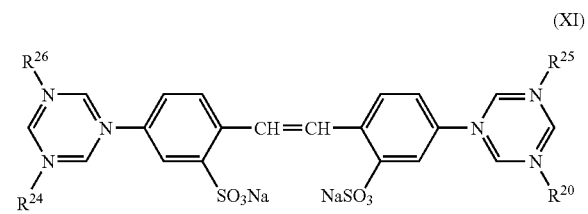

(XI)

in which
R$^{24}$, R$^{25}$ and R$^{26}$, independently of one another, represent —NH$_2$, —NH—CH$_3$, —NH-ethyl, —NH(—CH$_3$)$_2$, —NH-(ethyl)$_2$, —NHCH$_2$CH$_2$OH, —NH—C$_2$-C$_4$-hydroxyalkyl, —NH(C$_2$-C$_4$-hydroxyalkyl)$_2$, —NHCH$_2$CH$_2$SO$_3$H, —NH—CH$_2$CH$_2$OCH$_2$CH$_2$OH, —O—CH$_3$, —OCH—(CH$_3$)$_2$, —O—CH$_2$CH$_2$OCH$_3$, —N(CH$_2$CH$_2$OH)$_2$, —N(CH$_2$CHOH—CH$_3$)$_2$, morpholino, —S—CH$_3$, —N(CH$_2$CH$_2$OH)CH$_2$CH$_2$CONH$_2$ or a radical of the formula

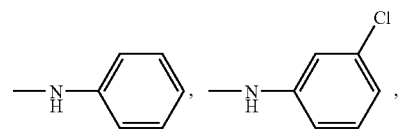

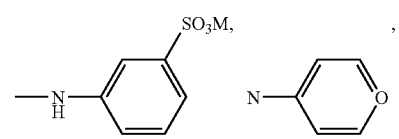

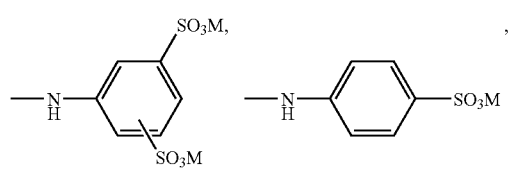

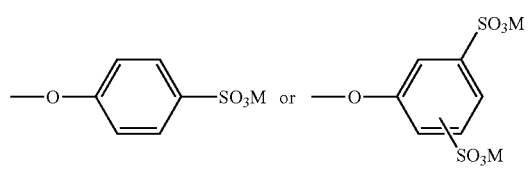

in which

R denotes hydrogen or $C_1$-$C_3$-alkyl and M has the meaning described above. Likewise particularly preferred are the triazine derivatives having the structure (XII).

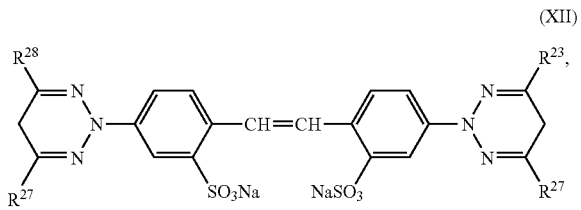

(XII)

in which $R^{27}$ and $R^{28}$, independently of one another, denote hydrogen, $C_1$-$C_3$-alkyl or phenyl.

The optional dispersant a3) preferably serves for better distribution of the essentially water-insoluble or sparingly soluble substance a2) emitting visible light on UV exposure.

In principle, all water-soluble polymeric dispersants are suitable for this purpose.

Polyvinyl ethers and polyvinyl esters and partial or complete hydrolysis products of the polyvinyl esters (Houben-Weyl, Methoden der organischen Chemie [Methods of organic chemistry], 4th Edition, Volume E 20, Part 2, pages 1195 to 1226), starch esters (Houben-Weyl, Methoden der organischen Chemie [Methods of organic chemistry], 4th Edition, Volume E 20, Part 3, pages 2151 to 2161) and starch ethers (Houben-Weyl, Methoden der organischen Chemie [Methods of organic chemistry], 4th Edition, Volume E 20, Part 3, pages 2138 to 2147) and starch ether esters (Houben-Weyl, Methoden der organischen Chemie [Methods of organic chemistry], 4th Edition, Volume E 20, Part 3, page 2151), cellulose ethers (Houben-Weyl, Methoden der organischen Chemie [Methods of organic chemistry], 4th Edition, Volume E 20, Part 3, pages 2086 to 2089) and cellulose esters (Houben-Weyl, Methoden der organischen Chemie [Methods of organic chemistry], 4th Edition, Volume E 20, Part 3, pages 2093 to 2123) and cellulose ether esters (Houben-Weyl, Methoden der organischen Chemie [Methods of organic chemistry], 4th Edition, Volume E 20, Part 3, page 2092) may be mentioned by way of example.

Biodegradable water-soluble polymeric dispersants a3) are preferred.

Polyvinyl alcohol is particularly preferred.

Suitable auxiliaries and additives a4) optionally to be added to the composition are, for example, flow control agents, free-flow agents, pigments, antifoams, deaerators, dyes, fillers, dulling agents, thickeners, emulsifiers, levelling agents such as those known to a person skilled in the art from the prior art.

The preparation of the composition is preferably effected by mixing the components a1) to a4) in water.

The actual use can be effected, for example, by applying the composition to the site to be monitored, preferably the traffic route, or to that part of the site which is to be marked. This is expediently effected by spraying with apparatuses according to the prior art. In the case of relatively small objects, the treatment liquor according to the invention can also be applied by spreading, brushing on or rolling on.

As a result of spraying with the composition, a cohesive strong film comprising a substance emitting visible light on UV exposure forms after drying on the traffic routes, such as, for example, roads, carriageways and paths, as well as railway lines or tram lines, but also plots, such as, for example, park, garden, woodland or other sites. Access by foot and by vehicle destroys or damages this film locally in the areas subjected to stress, so that, on UV exposure, these tracks can be visualized as defects. Thus, access by foot and/or access by vehicle and any other change can be determined.

In a particular embodiment, a composition which contains a biodegradable binder is applied so that aftertreatment can be effected at regular intervals and "old" and "new" damage to the film cannot lead to misinterpretations.

Thus, areas can be monitored for unauthorized access by foot and access by vehicle without this having to be effected in a time-consuming and labour-intensive manner. A further advantage is that detected changes can be monitored locally, and this is therefore also possible in a substantially less labour- and hence cost-intensive manner.

The method according to the invention is used for securing danger areas, such as, for example, military areas and security areas, military training grounds, public buildings and the immediate vicinity thereof, strategically important means of transport, such as bridges and crossings, locks, ship lifts and waterways, such as canals, railway lines and tram lines, in particular fast and high-speed zones, and electromagnetic railways, motorways and the immediate vicinity thereof, such as intersections and intersection-free facilities, such as motorway interchanges.

It is also possible to secure stocks in this way to prevent possible manipulations. The method according to the invention can also be used for securing movable objects, such as, for example, garden furniture or car radios, but also larger warehouses and quantities of goods, such as, for example, for bulk materials, such as coal or briquettes, in a heap or loaded onto cars, but also for high-quality goods present in packed form, such as, for example, television sets or electronic appliances in cartons or containers.

Here, the identification of moving objects is possible or detection on the basis of marked packaging (for example televisions, electronic appliances) or marked containers or by means of spilt transported material (for example coal).

A further application to be mentioned here by way of example is the marking of containers for determining manipulations of fastening or other security systems. Thus, for example, cabinets, desks, crates or else doors which are screwed together, nailed together or riveted together can be marked by the method according to the invention for determining unauthorized opening or for revealing breaking-open.

EXAMPLES

Raw materials:

Preparation of the Polymeric Adhesive 1:

1500 parts of a polyester of adipic acid with 1,6-hexanediol and neopentylglycol (OH number 65) are prepolymerized with 265 parts of hexamethylene diisocyanate until the isocyanate content is 3.3%. The prepolymer is then dissolved in 3360 parts of acetone.

86 parts of 45% strength solution of 2-aminoethyl-2-aminoethane sulphonic acid sodium salt ($NH_2CH_2CH_2HCH_2CH_2SO_3Na$) in water, 13.5 parts of ethylenediamine and 408 parts of water are then added to the solution in acetone and stirred in homogeneously.

After dilution with 2340 parts of water has been effected and the acetone distilled off, an approx. 40% strength dispersion results.

Optical brightener 1): Compound corresponding to structure (XII) with hydrogen as R 27 and phenyl as R 28.
Polymeric dispersant 1) Mowiol® 26-88 from Clariant.

Components of the Composition 1:

| | |
|---|---|
| 2 | parts by weight of the abovementioned optical brightener |
| 450 | parts by weight of the polymeric adhesive described above |
| 450 | parts by weight of an aqueous solution containing 0.05 part by weight of Mowiol ® 26-88 |
| 98 | parts by weight of demineralized water |

Component of the Composition 2:

| | |
|---|---|
| 2 | parts by weight of the abovementioned optical brightener |
| 450 | parts by weight of the polymeric adhesive described above |
| 450 | parts by weight of an aqueous solution containing 0.05 part by weight of Mowiol ® 26-88 |
| 20 | parts by weight of ACE Matt ® OK 412 (dulling agent from Degussa) |
| 78 | parts by weight of demineralized water |

Components of the Aqueous Composition 3:

| | |
|---|---|
| 2 | parts by weight of the abovementioned optical brightener |
| 450 | parts by weight of the polymeric adhesive described above |
| 450 | parts by weight of an aqueous solution containing 0.05 part by weight of Mowiol ® 26-88 |
| 5 | parts by weight of Acramin ® Black FBB (a pigment formulation from Dystar) |
| 93 | parts by weight of demineralized water |

Test:

The compositions 1, 2 and 3 prepared according to the abovementioned formulation were each sprayed by means of a flower spray onto a 1 m×1 m square with track ballast, gravel or fine aggregate.

After drying of the aqueous layer, the respective layers were walked on briefly by a test subject.

Exposure to a portable UV lamp both before and after the test surfaces had been walked on gave a readily distinguishable difference in optical impression in all cases. The traces can be very readily identified.

We claim:

1. A method for determining changes of a site, comprising:
   a) treating the site with a composition;
   b) exposing the site thus treated, an untreated site or combinations thereof to UV light; and
   c) determining a deviation of an intensity of emitted light from the site immediately following treatment and a light intensity of emitted light from the site at a later time,
   wherein the composition is an aqueous dispersion having:
      a1) at least one binder is selected from a biodegradable water-dispersable polyurethane binder, a polymeric film forming binder, and combinations thereof;
      a2) at least one substance that emits visible light upon exposure to UV light; and
      a3) optionally, a dispersant.

2. The method of claim 1, wherein the biodegradable, water-dispersable polyurethane binder comprises:
   a diisocyanate having 4 to 50 carbon atoms;
   a diol having a molecular weight of 500 to 4,000 g/ml selected from polyesterdiols;
   a diol, diamine, or triamine chain extender having a molecular weight of 62 to 500 g/mol or a combination of diol, diamine, and triamine chain extenders;
   a monol, polyol, monoamine or polyamine having primary or secondary amino groups or combinations thereof and at least one group having a hydrophilizing effect.

3. A method of improving the interpretability of emitted light when determining changes of a site comprising:
   employing the method of claim 1 wherein the binder is a biodegradable water dispersable polyurethane.

4. The method of claim 1, wherein movement within or around the site is observed by monitoring the deviation over time.

5. A site marked by the method comprising:
   a) treating the site with a composition;
   b) exposing the site thus treated, an untreated site or combinations thereof to UV light; and
   c) determining a deviation of an intensity of emitted light from the site immediately following treatment and a light intensity of emitted light from the site at a later time,
   wherein the composition is an aqueous dispersion having:
      a1) at least one binder is selected from a biodegradable water-dispersable polyurethane binder, a polymeric film forming binder, and combinations thereof;
      a2) at least one substance that emits visible light upon exposure to UV light; and
      a3) optionally, a dispersant.

6. A method for marking a site, comprising:
   a) treating the site with a composition;
   b) exposing the site thus treated, an untreated site or combinations thereof to UV light;
   c) observing emitted light from the site so treated; and
   d) repeating step c) intermittently,
   wherein the composition is an aqueous dispersion having:
      a1) at least one binder selected from a biodegradable water-dispersable polyurethane binder, polymeric film forming binder and combinations thereof;
      a2) at least one substance that emits visible light upon exposure to UV light; and
      a3) optionally, a dispersant.

7. The method of claim 6, wherein movement within or around the site is observed by monitoring changes in the emitted light between intermittent observations.

8. A site marked by the method comprising:
   a) treating the site with a composition;
   b) exposing the site thus treated, an untreated site or combinations there of to UV light;
   c) observing emitted light from the site so treated; and
   d) repeating step c) intermittently,
   wherein the composition is an aqueous dispersion having:
      a1) at least one binder selected from a biodegradable water-dispersable polyurethane binder, polymeric film forming binder and combinations
      a2) at least one substance that emits visible light upon exposure to UV light; and
      a3) optionally, a dispersant.

9. A method for determining changes of a site, comprising:
   a) treating the site with a composition;
   b) exposing the site thus treated, an untreated site or combinations thereof to UV light; and
   c) determining a deviation of an intensity of emitted light from the site immediately following treatment and a light intensity of emitted light from the site at a later time, wherein the composition is an aqueous dispersion having:
- a1) at least one binder is selected from a biodegradable water-dispersable polyurethane binder, a polymeric film forming binder, and combinations thereof, wherein the film forming binder is prepared by polymerization in an aqueous solution;
- a2) at least one substance that emits visible light upon exposure to UV light; and
- a3) optionally, a dispersant.

10. The method of claim 9, wherein the polymerization comprises the polymerization of a acrylomido homo- and copolymer wherein the comonomer is selected from acrylamide; methacrylamide; styrene; acrylic acid; methyl, ethyl, butyl and 2-ethylhexyl (meth)acrylate; or combinations thereof.

11. The method of claim 9, wherein the polymerization comprises an emulsion copolymerization of monomers selected from methyl, ethyl, butyl and 2-ethylhexyl (meth)acrylate, and combinations thereof and monomers selected from styrene, acrylonitrile, acrylic acid, actylamide, methacrylamide and combinations thereof.

* * * * *